(12) United States Patent
Calhoun et al.

(10) Patent No.: US 10,967,067 B2
(45) Date of Patent: Apr. 6, 2021

(54) SCAVENGER RECEPTOR UPTAKE FOR FABRY DISEASE ENZYME REPLACEMENT THERAPY

(71) Applicant: RESEARCH FOUNDATION OF THE CITY UNIVERSITY OF NEW YORK, New York, NY (US)

(72) Inventors: David H. Calhoun, Leonia, NJ (US); Lane Gilchrist, Brooklyn, NY (US)

(73) Assignee: RESEARCH FOUNDATION OF THE CITY UNIVERSITY OF NEW YORK, New York, NY (US)

(*) Notice: Subject to any disclaimer, the term of this patent is extended or adjusted under 35 U.S.C. 154(b) by 100 days.

(21) Appl. No.: 16/201,796

(22) Filed: Nov. 27, 2018

(65) Prior Publication Data

US 2019/0083639 A1 Mar. 21, 2019

Related U.S. Application Data

(63) Continuation-in-part of application No. 13/970,551, filed on Aug. 19, 2013, now Pat. No. 10,138,474.

(60) Provisional application No. 61/684,533, filed on Aug. 17, 2012.

(51) Int. Cl.
*A61K 47/64* (2017.01)
*A61K 9/00* (2006.01)
*C12N 9/40* (2006.01)
*A61K 38/47* (2006.01)
*A61K 47/60* (2017.01)
*A61K 9/127* (2006.01)

(52) U.S. Cl.
CPC .......... *A61K 47/643* (2017.08); *A61K 9/0085* (2013.01); *A61K 38/47* (2013.01); *A61K 47/60* (2017.08); *C12N 9/2465* (2013.01); *C12Y 302/01022* (2013.01); *A61K 9/1271* (2013.01)

(58) Field of Classification Search
CPC .... A61K 47/643; A61K 47/60; A61K 9/0085; A61K 38/47; A61K 9/1271; C12Y 302/01022; C12N 9/2465
See application file for complete search history.

*Primary Examiner* — Robert S Cabral
(74) *Attorney, Agent, or Firm* — Hoffmann & Baron, LLP

(57) ABSTRACT

The present invention relates to a composition comprising a lysosomal enzyme conjugated to a negatively charged scavenger receptor ligand. In some embodiments, the lysosomal enzyme is conjugated to the scavenger receptor ligand by way of a linker. The present invention also relates to a composition comprising lysosomal enzyme encapsulated by a liposome, said liposome externally comprising a negatively charged scavenger receptor ligand. The invention further encompasses a method of treating a lysosomal storage disease with the compositions listed above. The ionvention further encompasses a method of treating a lysosomal storage disease with an acylated, acetylated, or aconitylated lysosomal enzyme.

8 Claims, 9 Drawing Sheets
(9 of 9 Drawing Sheet(s) Filed in Color)
Specification includes a Sequence Listing.

SEQUENCE LISTING

<160> NUMBER OF SEQ ID NOS: 3

<210> SEQ ID NO 1

```
<211> LENGTH: 429
<212> TYPE: PRT
<213> ORGANISM: Homo sapiens

<400> SEQUENCE: 1

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
```

| | | | |
|---|---|---|---|
| 385 | 390 | 395 | 400 |

Ser Arg Leu Arg Ser His Ile Asn Pro Thr Gly Thr Val Leu Leu Gln
                          405                     410                   415

Leu Glu Asn Thr Met Gln Met Ser Leu Lys Asp Leu Leu
                  420                   425

<210> SEQ ID NO 2
<211> LENGTH: 1290
<212> TYPE: DNA
<213> ORGANISM: Homo sapiens

<400> SEQUENCE: 2

| | |
|---|---|
| atgcagctga ggaacccaga actacatctg gctgcgcgc ttgcgcttcg cttcctggcc | 60 |
| ctcgtttcct gggacatccc tggggctaga gcactggaca atggattggc aaggacgcct | 120 |
| accatgggct ggctgcactg ggagcgcttc atgtgcaacc ttgactgcca ggaagagcca | 180 |
| gattcctgca tcagtgagaa gctcttcatg gagatggcag agctcatggt ctcagaaggc | 240 |
| tggaaggatg caggttatga gtacctctgc attgatgact gttggatggc tccccaaaga | 300 |
| gattcagaag gcagacttca ggcagaccct cagcgctttc ctcatgggat tcgccagcta | 360 |
| gctaattatg ttcacagcaa aggactgaag ctagggattt atgcagatgt ggaaataaa | 420 |
| acctgcgcag gcttccctgg agttttgga tactacgaca ttgatgccca gacctttgct | 480 |
| gactggggag tagatctgct aaaatttgat ggttgttact gtgacagttt ggaaatttg | 540 |
| gcagatggtt ataagcacat gtccttggcc ctgaatagga ctggcagaag cattgtgtac | 600 |
| tcctgtgagt ggcctcttta tgtgtggccc tttcaaaagc ccaattatac agaaatccga | 660 |
| cagtactgca atcactggcg aaattttgct gacattgatg attcctggaa agtataaag | 720 |
| agtatcttgg actggacatc ttttaaccag gagagaattg ttgatgttgc tggaccaggg | 780 |
| ggttggaatg acccagatat gttagtgatt ggcaactttg gcctcagctg aatcagcaa | 840 |
| gtaactcaga tggccctctg gctatcatg gctgctcctt tattcatgtc taatgacctc | 900 |
| cgacacatca gccctcaagc caaagctctc cttcaggata aggacgtaat tgccatcaat | 960 |
| caggaccct tgggcaagca agggtaccag cttagacagg gagacaactt gaagtgtgg | 1020 |
| gaacgacctc tctcaggctt agcctgggct gtagctatga taaaccggca ggagattggt | 1080 |
| ggacctcgct cttataccat cgcagttgct tccctgggta aggagtggc ctgtaatcct | 1140 |
| gcctgcttca tcacacagct cctccctgtg aaaaggaagc tagggttcta tgaatggact | 1200 |
| tcaaggttaa gaagtcacat aaatcccaca ggcactgttt tgcttcagct agaaaataca | 1260 |
| atgcagatgt cattaaaaga cttactttaa | 1290 |

<210> SEQ ID NO 3
<211> LENGTH: 1418
<212> TYPE: DNA
<213> ORGANISM: Homo sapiens

<400> SEQUENCE: 3

| | |
|---|---|
| aaacaataac gtcattattt aataagtcat cggtgattgg tccgcccctg aggttaatct | 60 |
| taaaagccca ggttacccgc ggaaatttat gctgtccggt caccgtgaca atgcagctga | 120 |
| ggaacccaga actacatctg gctgcgcgc ttgcgcttcg cttcctggcc ctcgtttcct | 180 |
| gggacatccc tggggctaga gcactggaca atggattggc aaggacgcct accatgggct | 240 |
| ggctgcactg ggagcgcttc atgtgcaacc ttgactgcca ggaagagcca gattcctgca | 300 |
| tcagtgagaa gctcttcatg gagatggcag agctcatggt ctcagaaggc tggaaggatg | 360 |

```
caggttatga gtacctctgc attgatgact gttggatggc tccccaaaga gattcagaag      420
gcagacttca ggcagaccct cagcgctttc ctcatgggat tcgccagcta gctaattatg      480
ttcacagcaa aggactgaag ctagggattt atgcagatgt tggaaataaa acctgcgcag      540
gcttccctgg gagttttgga tactacgaca ttgatgccca gacctttgct gactggggag      600
tagatctgct aaaatttgat ggttgttact gtgacagttt ggaaaatttg gcagatggtt      660
ataagcacat gtccttggcc ctgaatagga ctggcagaag cattgtgtac tcctgtgagt      720
ggcctcttta tatgtggccc tttcaaaagc ccaattatac agaaatccga cagtactgca      780
atcactggcg aaattttgct gacattgatg attcctggaa aagtataaag agtatcttgg      840
actggacatc ttttaaccag gagagaattg ttgatgttgc tggaccaggg ggttggaatg      900
acccagatat gttagtgatt ggcaactttg gcctcagctg gaatcagcaa gtaactcaga      960
tggccctctg ggctatcatg gctgctcctt tattcatgtc taatgacctc cgacacatca     1020
gccctcaagc caaagctctc cttcaggata aggacgtaat tgccatcaat caggacccct     1080
tgggcaagca agggtaccag cttagacagg gagacaactt tgaagtgtgg gaacgacctc     1140
tctcaggctt agcctgggct gtagctatga taaaccggca ggagattggt ggacctcgct     1200
cttataccat cgcagttgct tccctgggta aaggagtggc ctgtaatcct gcctgcttca     1260
tcacacagct cctccctgtg aaaaggaagc tagggttcta tgaatggact tcaaggttaa     1320
gaagtcacat aaatcccaca ggcactgttt tgcttcagct agaaaataca atgcagatgt     1380
cattaaaaga cttactttaa aatgtttatt ttattgcc                            1418
```

SCAVENGER RECEPTOR UPTAKE FOR FABRY DISEASE ENZYME REPLACEMENT THERAPY

This application is a continuation-in-part of U.S. patent application Ser. No. 13/970,551 filed on Aug. 19, 2013, which claims the benefit of priority of U.S. Patent Application No. 61/648,533, filed on Aug. 17, 2012, all of which are incorporated herein by reference in their entirety.

This invention was made with government support under RCMI RR03060 awarded by National Institutes of Health (NIH). The government has certain rights in the invention.

BACKGROUND OF THE INVENTION

Lysosomal storage diseases result from an inherited trait which affects the levels of enzymes in the lysosome. Approximately 30 lysosomal storage diseases are known to affect humans. Tay-Sach's disease and Gaucher disease are members of this group of diseases. Since specific pathways for the uptake of these other lysosomal enzymes also exist, enzyme replacement therapy is expected to be effective in Fabry disease and could logically be expected to be successful in these other diseases as well. Although these diseases are individually rare, (e.g., several thousand patients with Fabry disease are known to occur world wide, i.e., 1 to 40,000), as a group this class of diseases accounts for a significant fraction of all inherited diseases.

Fabry disease is one such lysosomal storage disease known to affect humans. Fabry disease is an X-linked inborn error of metabolism resulting from a deficiency of the lysosomal enzyme, α-galactosidase A. Deficiency of α-galactosidase A results in the accumulation of its major glycosphingolipid substrate, globotriaosylceramide and related glycolipids with terminal α-galactosidic linkages. Progressive substrate deposition, especially in the plasma and vascular endothelium, leads to ischemia and infarction with early demise due to vascular disease of the heart, kidney, and brain.

Enzyme replacement therapy was first suggested by De Duve et al. (See De Duve et al. 1964, Federation Proceedings 23:1045) as a possible approach to the treatment of lysosomal storage defects such as Fabry disease. Several lines of evidence suggest that enzyme replacement therapy may be beneficial for patients with Fabry disease. For example, it has been demonstrated in cell cultures of fibroblasts obtained from patients with this disease that enzyme present in the culture medium is specifically transported to lysosomes. Clinical trials of enzyme replacement therapy have been reported for patients with Fabry disease using infusions of normal plasma (Mapes et al., 1970, *Science* 169: 987-989); α-galactosidase A purified from placenta (Brady et al., 1973, *New Eng. J. Med.* 279: 1163); or α-galactosidase A purified from spleen or plasma (Desnick et al., 1979, *Proc. Natl. Acad. Sci. USA* 76: 5326-5330). In one study (Desnick et al.) intravenous injection of purified enzyme resulted in a transient reduction in the plasma levels of the substrate, globtriaosylceramide.

Since the initial studies of enzyme replacement therapy as a potential treatment for Fabry disease, Calhoun et al. have isolated human α-galactosidase A cDNA (Calhoun et al. 1985, Proc Natl Acad Sci USA 82:7364-8) and genomic clones (Quinn et al. 1987, *Gene* 58:177-88), and expressed the cDNAs in bacteria (Hantzopoulos et al. 1987, *Gene* 57:159-69), insect cells (Chen et al. 2000, *Protein Expr Purif* 20:228-36; Coppola et al. 1994, *Gene* 144:197-203), and *Pichia pastoris* (Chen et al. 2000, *Protein Expr Purif* 20:472-84). Furthermore, the purified recombinant α-galactosidase A produced in insect cells and *P. pastoris* has been shown to be taken up by Fabry fibroblasts in cell culture.

Several clinical trials of enzyme replacement therapy for Fabry disease patients in the last few years revealed clinical efficacy. Furthermore, the FDA has approved treatment of Fabry disease through intravenous administration of recombinant α-galactosidase A. This treatment methodology is known as enzyme replacement therapy (ERT). ERT does not affect the underlying defect, but provides a functional enzyme for the cell. Currently, two galactosidase drugs are available for treatment of Fabry disease via enzyme replacement therapy (ERT): agalsidase alfa (Replagal®, TKT/Shire) and agalsidase beta (Fabrazyme®, Genzyme). These protein based therapeutics are administered by (approved for) intravenous injection and deliver galactosidase activity to the lysomomes of affected organs in order to reduce the level of globotriaosylceramide accumulation.

However, the current approaches for enzyme replacement therapy can be expected to have limitations 88% of patients developed potentially neutralizing IgG antibodies to α-galactosidase A (Fabrazyme®) with a therapeutic enzyme dose of 1 mg per kilogram of body weight (Eng et al. 2001, *N. Engl. J. Med.* 345: 9-16); while only 21% developed antibodies with a lower dose of 0.2 mg of enzyme (Replagal®) per kilogram of body weight, (Schiffmann et al. 2001, *JAMA* 285:2743-9).

Fabry disease patients with adverse reactions to the infusions are currently treated with antihistamines and antipyretics, but it can be anticipated that life-long treatment required for these patients will lead to unacceptable levels of neutralizing antibodies. Furthermore, the treatment regimen is burdensome. Infusions typically involve a 4-6 hours session, in a hospital setting, every other week for life. In a recent clinical trial 14 out of 58 patients had to withdraw due to serious noncompliance, voluntary withdrawal, serious adverse events leading to death due to heart or kidney disease due to symptoms from the disease, and IgE antibody or positive skin tests. See Germain D P et al. 2007, *J. Am. Soc. Nephrol.*, 18(5):1547-57. Most patients suffer from ill-defined infusion-associated reactions (vomiting, rigors, etc.) and are routinely pretreated with acetaminophen and hydroxyzine, and some patients require ibuprofen, prednisone, or both, for infusion associated reactions. Any improvement in treatment that leads to lower doses of enzyme, more effective therapeutic effects, or less frequent infusions would markedly improve the lives of Fabry disease patients and other patients reeving enzyme replacement therapy for lysosomal storage diseases.

Hence there exists a long standing need to provide a treatment regimen that requires lower doses of enzyme, thereby providing for more effective therapeutic effects and less frequent infusions. In particular, there is a need to provide an enzyme therapeutic that allow for targeted delivery within the body and are sufficiently biologically active upon intracellular uptake.

SUMMARY OF THE INVENTION

The present invention relates to a composition comprising a lysosomal enzyme conjugated to a negatively charged scavenger receptor ligand. In some embodiments the lysosomal enzyme is an enzyme listed in TABLE 2, and the negatively charged scavenger receptor ligand is any ligand that binds a scavenger receptor and is transported to the lysosome.

In some embodiments, the lysosomal enzyme is conjugated to the scavenger receptor ligand by way of a linker.

The present invention also relates to a composition comprising lysosomal enzyme encapsulated by a liposome, said liposome externally comprising a negatively charged scavenger receptor ligand.

The invention further encompasses a method of treating a lysosomal storage disease with the compositions listed above.

The invention further encompasses a method of treating a lysosomal storage disease with an acylated, acetylated, or aconitylated lysosomal enzyme.

The invention further encompasses a composition and method for delivering a compound across the blood brain barrier, said method includes conjugating a compound to a blood brain barrier transporter targeting moiety, to provide a conjugated compound; and contacting the conjugated compound with the blood brain barrier.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION

Figure 1:
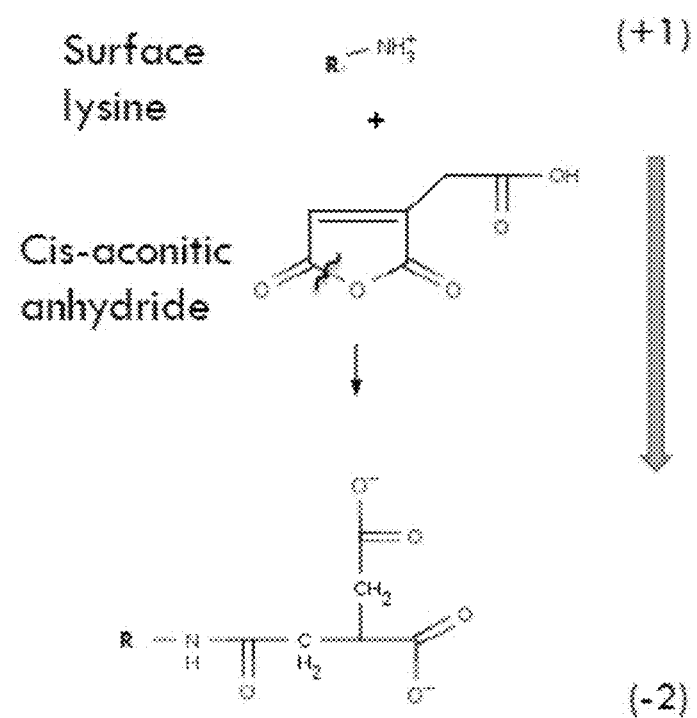
FIG. 1 depicts the reaction between cis-aconitic anhydride and an amino group of a surface exposed lysine. Cis-aconitic anhydride coupling to Lys residues introduces a net three negative charges for each Lys residue. TNBSA (2,4,6-trinitrobenzene sulfonic acid) and fluorescamine were used to measure free surface Lys residues on α-Gal A.
Figure 2:
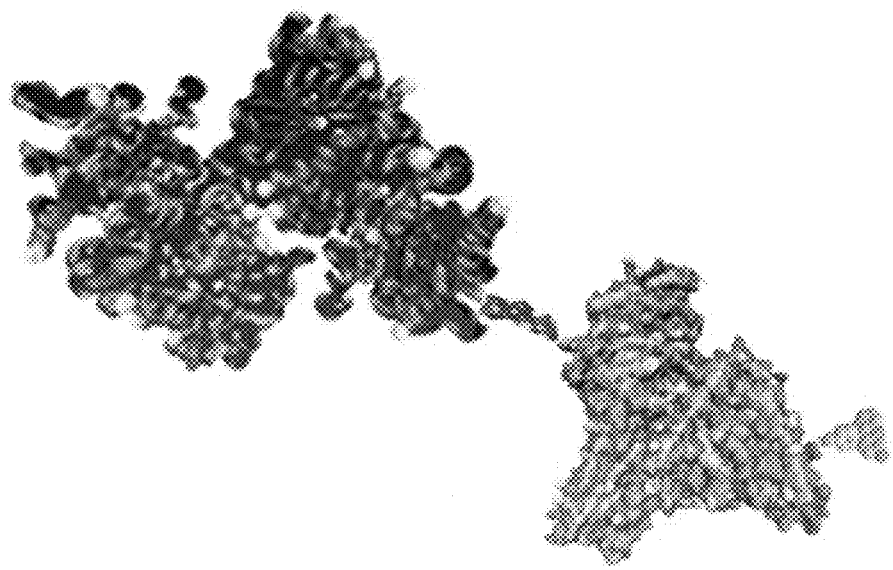
FIG. 2 depicts α-galactosidase A with hydrolyzable polymer linkage to acylated and labeled human serum albumin.

The present invention is directed to compositions and methods relating to the enhanced delivery of lysosomal storage disease related agents to the lysosomes of cells affected by lysosomal storage disease.

In the following description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

In one aspect, the invention relates to a composition that includes a lysozomal enzyme or an active fragment thereof, or the variant of said protein conjugated to a negatively charged scavenger receptor ligand.

A lysosomal enzyme as defined herein is any enzyme in the lysosome which hydrolyzes or metabolizes substrates in the lysosome. Lysozomal enzymes are commonly known. See TABLE 2, and www.ncbi.nlm.nih.gov/books/NBK6177/ (which is hereby incorporated by reference in its entirety). Examples of lysozomal enzymes include digestive enzymes such as glycosidases, proteases, and sulfatases. Examples of glycosidases include α-galactosidase A and heparinase. Examples of proteases include cathepsin K. Examples of sulfatases include iduronate sulfatase and N-acetyl glucosaminidase.

A lysosomal enzyme as defined herein to include an active fragment or variant thereof. By active fragments, or variants, is meant any part of the enzyme which is derived from the intact whole enzyme and still retains biological activity. Likewise, derivatives or variants of lysosomal enzyme mean enzymes which have been chemically modified or genetically engineered to effect minor changes, for example amino acid substitutions, which maintain biological activity.

In a preferred embodiment, the lysosomal enzyme is α-galactosidase A. α-galactosidase A is also a known protein. See ENZYME entry: EC 3.2.1.22, NCBI; and Calhoun et al. 1985, *Proc. Natl. Acad. Sci.* USA 82:7364-8. The α-galactosidase A protein is a lysosomal enzyme which hydrolyzes globotriaosylceramide and related glycolipids which have terminal α-galactosidase linkages. It is a 45 kDa N-glycosylated protein encoded on the long arm of the X chromosome. The initial glycosylated forms (Mr=55,000 to 58,000) synthesized in human fibroblasts or Chang liver cells are processed to a mature glycosylated form (Mr=50,000). The mature active enzyme as purified from human tissues and plasma is a homodimer. (Bishop et al. 1986, *Proc. Natl. Acad. Sci. USA* 83: 4859-4863).

A human liver cDNA for α-galactosidase A was identified in a λgt11 expression library (Calhoun et al., 1985, *Proc. Natl. Acad. Sci. USA* 82: 7364-7368), and its sequence reported by Bishop et al. The original cDNA isolated by Calhoun et al. (1985) encoded the mature amino acid sequence of α-galactosidase A. See Calhoun et al., 1985, *Proc. Natl. Acad. Sci. USA* 82: 7364-7368. These references are hereby incorporated by reference in its entirety.

α-galactosidase A can be derived from a natural source or be derived synthetically. In addition, α-galactosidase A, as defined herein can include an active fragment thereof, or include active variants. By active fragments, or variants, is meant any part of the enzyme which is derived from the intact whole enzyme and still retains biological activity. Likewise, derivatives or variants of lysosomal enzyme mean enzymes which have been chemically modified or genetically engineered to effect minor changes, for example amino acid substitutions, which maintain biological activity. As defined herein, biological activity of α-galactosidase A is the ability to hydrolyze globotriaosylceramide and related glycolipids which have terminal α-galactosidase linkages.

The α-galactosidase A utilized in the invention may be obtained using any method known to a person skilled in the art. It is thus possible to obtain the α-galactosidase A, a fragment thereof, or the variant of said protein by any standard method. For example, α-galactosidase A may be obtained from cDNA by means of expression in a heterologous organism such as, for example, *Escherichia coli, Sacharomyces cerevisiae, Pichia pastoris*. For example, U.S. Pat. No. 5,658,567 to Calhoun et al. describes a method of obtaining recombinant α-galactosidase A; which is herein incorporated by reference in its entirety. Additional information may be found in U.S. Pat. Nos. 5,179,023; 6,461,609; and 7,011,831, each of which is hereby incorporated by reference in its entirety.

In one embodiment, the lysozomal enzyme is engineered to confer additional negative charge to the enzyme. Additional negative charge may be conferred by substituting WT amino acid residues with negatively charged residues. Negatively charged residues include aspartic acid and glutamic acid.

WT sequence for α-galactosidase A (uniprot P06280).

In another embodiment, the surface exposed WT lysine residues may be reacted with

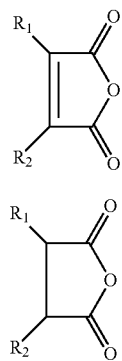

$R_1$ and $R_2$ are independently H, OH, COOH, $(CH_2)_nOH$, $(CH_2)_nCH_3$, $CH_3$, $CH_2CO_2H$, $(CH_2)_nCO_2H$, or $(CH_2)_2COSCH_2CO_2H$.

n is 1-10

The WT lyxozomal enzyme may be α-galactosidase A, α-sialidase, α-mannosidase, β-mannosidase, glycosylasparaginase, α-fucosidase, α-N-acetylglucosaminidase, β-galactosidase, β-hexosaminidase, α-subunit, β-hexosaminidase β-subunit, glucocerebrosidase, arylsulfatase A, saposin B, formyl-glycin generating enzyme, β-galactosylceramidase, iduronate sulfatase, α-iduronidase, heparan N-sulfatase, acetyl-CoA transferase, N-acetyl glucosaminidase, β-glucuronidase, N-acetyl glucosamine 6-sulfatase, N-acetylgalactosamine 4-sulfatase, galactose 6-sulfatase, hyaluronidase, α-glucosidase, acid sphingomyelinase, acid ceramidase, acid lipase, cathepsin K, cathepsin A, tripeptidyl peptidase, or palmitoyl-protein thioesterase.

Chemical Modification.

Surface lysine residues on the lysosomal enzyme may be modified to confer additional negative charge.

In one embodiment, the lysoszomal enzyme is α-galactosidase A. At least 10%, at least 25%, at least 50%, at least 75%, at least 90% of the surface exposed lysine residues.

In another embodiment, the lysozomal enzyme may be engineered to include additional surface exposed lysine residues not found in the wild type lysosomal enzyme. For example, a surface non-lysine amino acid residue may be substituted with a lysine residue. The lysine residue may be modified to confer additional negative charge.

In one embodiment, the lysozomal enzyme is α-galactosidase A having one or more of the following mutations: N215K, N139K, N192K, S197K, V199K, S201K, C202K, W204K, P205K, Y207K, P210K, Q212K, P214K, Y216K, M208K, W209K, F211XK, Y134K, G138K, T141K, A190K, L191K, R193K, T194K, V137K, Y184K, S188K, S197K, and V199K.

The engineered α-galactosidase A having one of the aforementioned lysine mutations is reacted with a compound of formula I and II.

In another embodiment, the lysosomal enzyme may be acylated. Acylation of lysosomal may be accomplished by any standard method. For example, acylation of amino groups in proteins may be accomplished with acid anhydrides. Suitable acid anhydrides include, for example, citraconic anhydride, maleic anhydride, succinic anhydride, 3-hydroxyphthalic anhydride, trimellitic anhydride, methyltetrahydrophthalic anhydride, cis-aconitic anhydride, fatty acid anhydrides, hexahydrophthalic anhydride, and phthalic anhydride.

In another embodiment, the lysosomal enzyme may be acetylated. Acetylation of lysosomal enzyme may be accomplished by any standard method. For example, reacting the protein of interest with acetic anhydride or acetyl chloride.

In another embodiment, the lysosomal enzyme may be aconitylated. Aconitylation of lysosomal enzyme may be accomplished by any standard method. For example, reacting the protein of interest with cis-aconitic anhydride.

The lysosomal enzyme is conjugated to a charged scavenger receptor ligand (SRL). SRLs are commonly known in the art. SRLs are defined as any ligand that is capable of binding scavenger receptors and the resulting ligand undergoes receptor-mediated endocytosis leading to the degradation of ligand in the lysosome. For example, SRLs include, without limitation: polyanionic ligands, AcLDL, OxLDL, β-amyloid, molecular chaperones, ECM, AGE, apoptotic cells, activated B-cells, bacteria, HDL, LDL, OxLDL, VLDL, AGE, ECM, activated platelets, serum protein, BSA, and HSA. See TABLE 1 and Stephen et al. 2010, *Int. J. Hypertens.*, 646929. This publication is incorporated herein by reference in its entirety.

LDL is low density lipoprotein; VLDL, very low density lipoprotein; AcLDL is acetylated-low density lipoprotein; and OxLDL is oxidized-low density lipoprotein. HDL is high density lipoprotein.

β-amyloid is a peptide of 36-43 amino acids that is processed from the amyloid precursor protein (APP). This peptide is characterized as having the central sequence KLVFFAE. The core sequence can be present once or several times in a β-amyloid peptide.

Molecular chaperones are proteins that assist the noncovalent folding or unfolding and the assembly or disassembly of other macromolecular structures. Examples include heat shock proteins (Hsp70, Hsp90 and Hsp110), gp96 and calreticulin.

ECM is extracellular matrix. These ligands comprise components of the extracellular matrix, for example, glycated collagen IV.

AGE advanced glycation end products. AGE are a heterogeneous group of compounds linked to both oxidative stress and inflammation and they are found in many tissues. They are the result of modifications of proteins or lipids that become nonenzymatically glycated and oxidized after contact with aldose sugars. Some examples of these ligands include glycated hemoglobin A1c (HbA1c).

Apoptotic cells are cells that are undergoing or about to undergo apoptosis. One characteristic of apoptotic cells is increased phosphatidylserine (PS) on the cell surface as compared to non-apoptotic cells.

Activated B-cells, are B-cells that have undergone the binding of antigen to receptors on its cell surface which causes the cell to divide and proliferate.

In a preferred embodiment, the SRL is serum protein. In another preferred embodiment, the SRL is human serum albumin (HSA).

TABLE 1

Scavenger Receptor Ligands and Expression profiles.

| Class | Scavenger Receptor | Ligands | Expression profile | Involvement in CVD? |
|---|---|---|---|---|
| A | SR-A [SR-A1] | AcLDL, OxLDL, β-amyloid, molecular chaperones, ECM, AGE, apoptotic cells, activated B-cell, bacteria | Macrophages, mast cells, dendritic cells, endothelial cells, and smooth muscle cells; Brain capillary endothelium (SR-A3, SR-A5) | Yes - involved in OxLDL uptake by macrophages leading to foam cell formation |
| A | MARCO [SR-A6] | AcLDL, OxLDL, apoptoic cells, B cells, bacteria | Macrophages, dendritic cells | No |
| B | SR-B [SR-B1] | HDL, LDL, OxLDL, apoptotic cells | Monocytes/macrophages, hepatocytes, adipocytes, and heart; Brain capillary endothelium (SR-B1) | Reduces atherosclerosis through reverse cholesterol transport of HDL |
| B | CD36 [SR-B2] | AcLDL, OxLDL, HDL, LDL, VLDL, β-amyloid, AGE, apoptotic cells | Macrophages, platelets, adipocytes, epithelial cells, endothelial cells, renal proximal tubular cells, vascular structures in spleen, tonsil, lung, heart, brain, kidney, endothelial cells lining hepatic sinusoids, virtually all microvascular endothelial cells including skin | Yes - OxLDL uptake into macrophages leading to foam cell formation |
| E | LOX-1 [SR-E1] | OxLDL, molecular chaperones, ECM, AGE, apoptotic cells, activated platelets, bacteria | Endothelial and smooth muscle cells, macrophages, and platelets | Yes - OxLDL uptake in endothelial cells, leads to endothelial dysfunction |
| F | SRECI/II [SR-F1] | AcLDL, OxLDL, molecular chaperones, apoptotic cells | Endothelial cells and macrophages | Low levels of AcLDL uptake |
| G | SR-PSOX [SR-G] | OxLDL and bacteria | Macrophages, smooth muscle, dendritic, endothelial cells, and B and T cells | Yes - involved in OxLDL uptake in macrophages |
| H | FEEL-I/II [SR-H1] | AcLDL, molecular chaperones, ECM, AGE, bacteria | Monocytes/macrophages, endothelial cell | No known link |

SR-A: scavenger receptor class A,
AcLDL: acetylated low density lipoprotein,
OxLDL: oxidized low density lipoprotein,
ECM: extracellular matrix,
AGE: advanced glycation end products,
MARCO: macrophage receptor with collagenous structure,
HDL: high density lipoprotein,
LDL: low density lipoprotein,
VLDL: very low density lipoprotein,
LOX-1: lectin-like oxidized low density lipoprotein receptor-1,
FEEL-I/II: fasciclin, epidermal growth factor (EGF)-like, laminin-type EGF-like, and link domain-containing scavenger receptor-1.

Bacteria are unicellular organisms. Examples include *Staphylococcus aureus, Neisseria meningitides, Streptococcus pyogenes* and *Escherichia coli*.

Activated platelets are platelets which react to injury. For example, when the skin is broken, platelets are exposed to collagen, which causes them to activate. Platelet activation triggers the release of chemicals which cause additional platelets to activate.

Serum protein of the present invention is commonly known in the art. Total serum protein, purified serum protein components, or any combination of serum proteins may be used. In a preferred embodiment, bovine serum albumin (BSA) or human serum albumin (HSA) may be used. Serum proteins are commercially available from Sigma Aldrich. In In another preferred embodiment, the SRL is any ligand that binds to a Scavenger Receptor (SR) and undergoes receptor-mediated endocytosis leading to the delivery of ligand to the lysosome. Scavenger receptors are commonly known in the art. TABLE 1 sets forth different classes of known ligands and the scavenger receptor to which they bind. Scavenger Receptors (SR) are defined as a family of molecules sharing the ability to bind polyanionic ligands. For example, scavenger receptors include, without limitation, SR-AI; MARCO; SRCL; CD36; dSR-Cl; CD68; LOX-1; SREC-I; SREC-II; SR-PSOX FEEL-1, FEEL-2, CSR1, SCSRA5, SR-B1, LIMP2, SR-PSOX, CD163, CD163L1, CD5, and CD6. See TABLE 1, and Murphy et al. 2005, *Atherosclerosis* 182, 1-15. This publication is incorporated herein by reference in its entirety.

The SRLs conjugated to the lysosomal enzyme are negatively charged. Said negative charge may be naturally occurring, or conferred by chemical modification by any method known in the art. For example, said negative charge can be conferred by formaldehyde treatment. In another embodiment, the SRL may be oxidized by chemical modification by any method known in the art. For example, with treatment by $Cu^{2+}$.

In another embodiment, the SRL may be acylated. Acylation of SRL may be accomplished by any standard method. For example, acylation of amino groups in proteins may be accomplished with acid anhydrides. Suitable acid anhydrides include, for example, citraconic anhydride, maleic anhydride, succinic anhydride, 3-hydroxyphthalic anhydride, trimellitic anhydride, methyl-tetrahydrophthalic anhydride, cis-aconitic anhydride, fatty acid anhydrides, hexahydrophthalic anhydride, and phthalic anhydride.

In another embodiment, the SRL may be acetylated. Acetylation of lysosomal enzyme may be accomplished by any standard method. For example, reacting the protein of interest with acetic anhydride or acetyl chloride.

In another embodiment, the SRL may be aconitylated. Aconitylation of lysosomal enzyme may be accomplished by any standard method. For example, reacting the protein of interest with cis-aconitic anhydride by any standard method.

Conjugation of lysosomal enzyme to a SRL may be accomplished by any standard method commonly known in the art. For example, a lysine on a lysosomal enzyme may be modified with an adaptor molecule to introduce a reactive group, such as a thiol. For example, the lysine residue may be reacted with a thiolation reagent, such as N-succinimidyl S-acetylthioacetate (SATA) or 2-iminothiolane. The thiol (deprotected thiol in the case of SATA) may be reacted with the thiol group on the side chain of cysteine on the surface of a SRL.

In a further example, a cysteine on the surface of a SRL may be modified with an adaptor molecule to introduce a reactive group, such as a N-hydroxysuccinimide (NHS). For example, the cysteine residue may be reacted with Sulfosuccinimidyl-4-(N-maleimidomethyl) cyclohexane-1-carboxylate (Sulfo-SMCC). The modified amino acid residue may then be reacted with the amino groups of lysines on a lysosomal enzyme to form a SRL—lysosomal enzyme conjugate.

Other conjugation techniques and strategies commonly known in the art may be used. Further conjugation techniques and strategies commonly known in the art are described in Hermanson, G., T. *Bioconjugate Techniques, Second Edition;* Academic Press: San Diego, Calif., 2008; which is herein incorporated by reference in its entirety.

In another aspect of the invention, the scavenger receptor ligand is conjugated to a lysosomal enzyme by way of a linker. The linker serves to covalently bind the lysosomal enzyme to the negatively charged scavenger receptor ligand. Any linker commonly known in the art may be used. In a preferred embodiment, the linker is non-absorbing, soluble, and hydrophilic linker. Non-absorbing is defined as being as a characteristic wherein the linker does not non-specifically bind protein, or does not illicit an immune reaction.

In another embodiment, the linker comprises a polysaccharide. An example of polysaccharide linker includes: hyaluronate, hyaluronic acid, heparin, chondroitin sulfate, chitosan, cellulose, dextran and alginic acid.

In another embodiment, the linker comprises a polyamine.

In another embodiment, the linker comprises poly(glycerol) (PG) and hyperbranched PG(HPG); poly(2-oxazoline)s, include poly(2-methyl-2-oxazoline (PMeoX) and poly(2-ethyl-2-oxazoline (PEtOX); poly(acrylamide), poly (vinylpyrrolidone (PVP), and poly (N-(2-hydroxypropyl) methacrylamide (PHPMA).

In another embodiment, the linker comprises a polyamino acid. For example, a polyamino acid may comprise poly glutamic acid (PGA); poly(hydroxyethyl-L-asparagine (PHEA); and poly(hydroxyethyl-L-glutamine (PHEG).

In another embodiment, the linker comprises polyethylene glycol (PEG). Some examples of PEG include linear or branched (multi-arm or star) structures.

Examples of multi-arm PEG polymers include comb and brush PEG polymers. A comb PEG is a branched PEG comprising two or more three-way branch points and linear side chains emanating from a main backbone polymer chain. A brush PEG is a branched PEG comprising three or more linear polymer chains emanating from a main backbone polymer chain.

In another preferred embodiment, the linker is star PEG. A star PEG, without limitation, is a branched PEG comprising three or more linear polymer chains emanating from a central core group or a single branch point. Examples of star shaped PEG polymers include, without limitation, 3, 4, 5, 6, 7, 8, 9, 10, and 11-arm star PEG polymers. PEG linkers are commonly known in the art and are commercially available from several commercial vendors including Sigma-Aldrich, NANOCS, and Creative PEGWorks.

In standard nomenclature, a branched PEG can be referred to by the number of polymer chains. Thus, a branched PEG having three polymer chains is referred to as a three-arm PEG or 3-arm PEG, a branched PEG having four polymer chains is referred to as a four-arm PEG or 4-arm PEG, a branched PEG having five polymer chains is referred to as a five-arm PEG or 5-arm PEG, a branched PEG having six polymer chains is referred to as a six-arm PEG or 6-arm PEG, a branched PEG having seven polymer chains is referred to as a seven-arm PEG or 7-arm PEG, etc. The physical properties of PEG, such as melting point, cohesiveness, and viscosity, can be altered by varying the length of the polymer chain, the type of initiator used during the polymerization process, and/or whether the PEG has a linear or branched configuration. PEG molecules, both linear and branched, are commercially available over a wide range of molecular weights from 300 g/mol to 10,000,000 g/mol.

Multi-arm polyethylene glycol is advantageous over the linear (straight-chain) polyethylene glycol in that multiarm PEG allows for a plurality of substituents. Straight-chain polyethylene glycol derivatives with two functional groups can only carry two molecules, while the multi-arm polyethylene glycol has several end groups, and thus has more than one active molecule connection points, and can carry several similar or different molecules.

Figure 3:
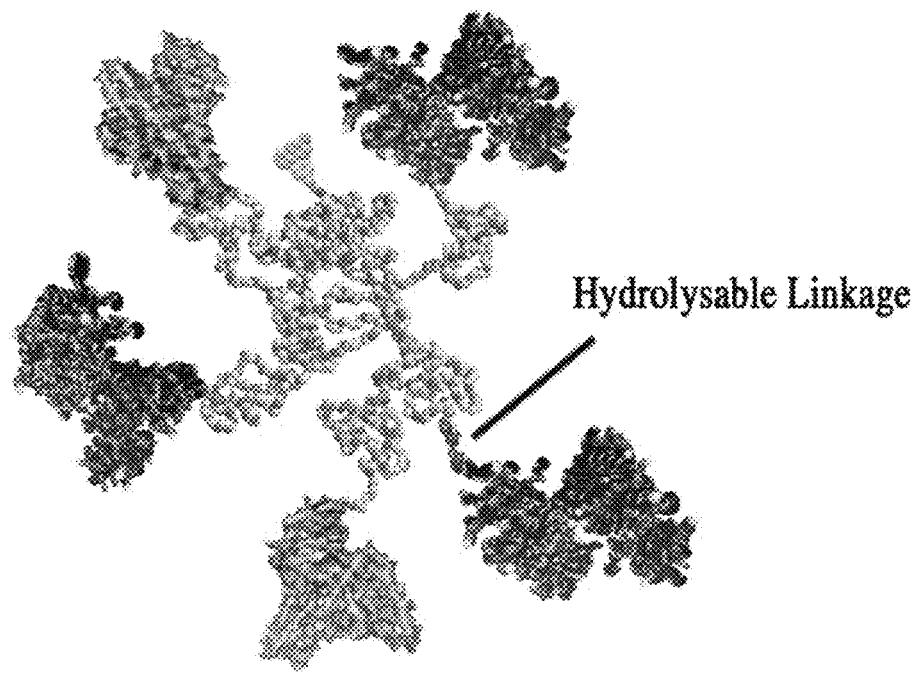
FIG. 3 depicts α-galactosidase A linked to 8-arm PEG with targeting and fluorescent group.
Figure 4:
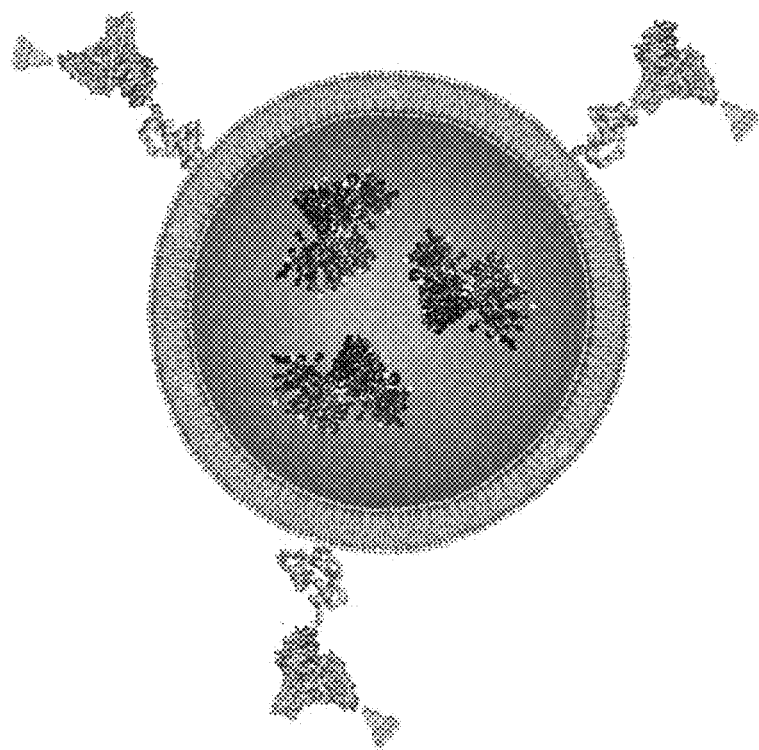
FIG. 4 depicts α-galactosidase A encapsulated in liposome with external surface conjugated with fluorescently labeled and aconitylated-HSA.
Figure 5:
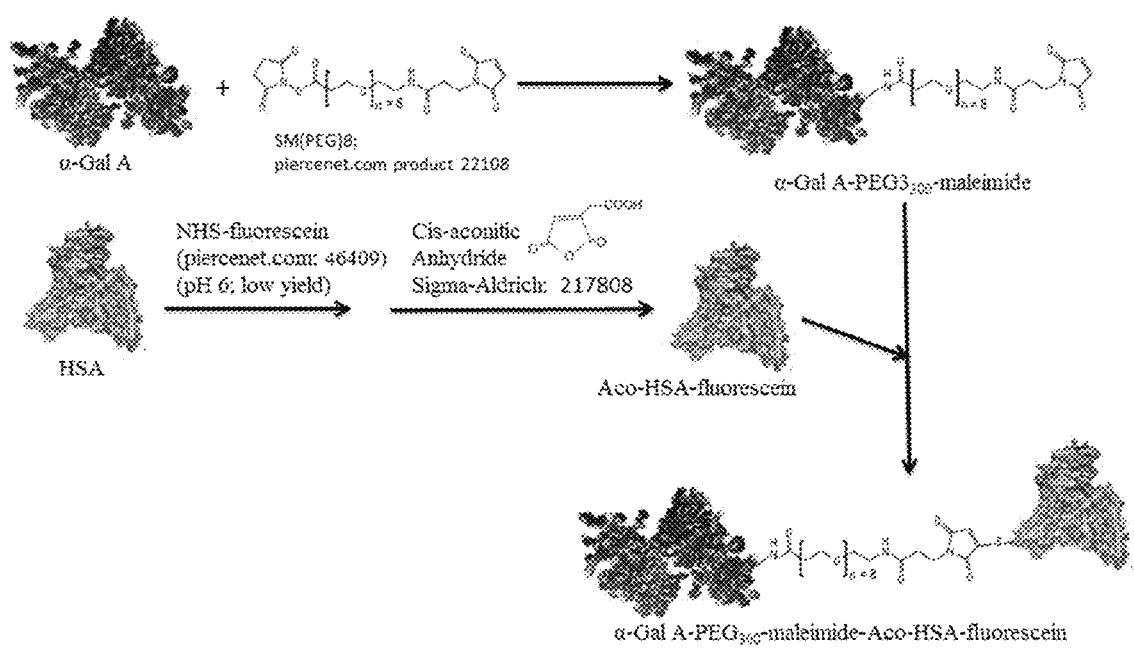
FIG. 5 depicts α-galactosidase A coupled to fluorescently labeled, aconitylated-HSA.
Figure 6:
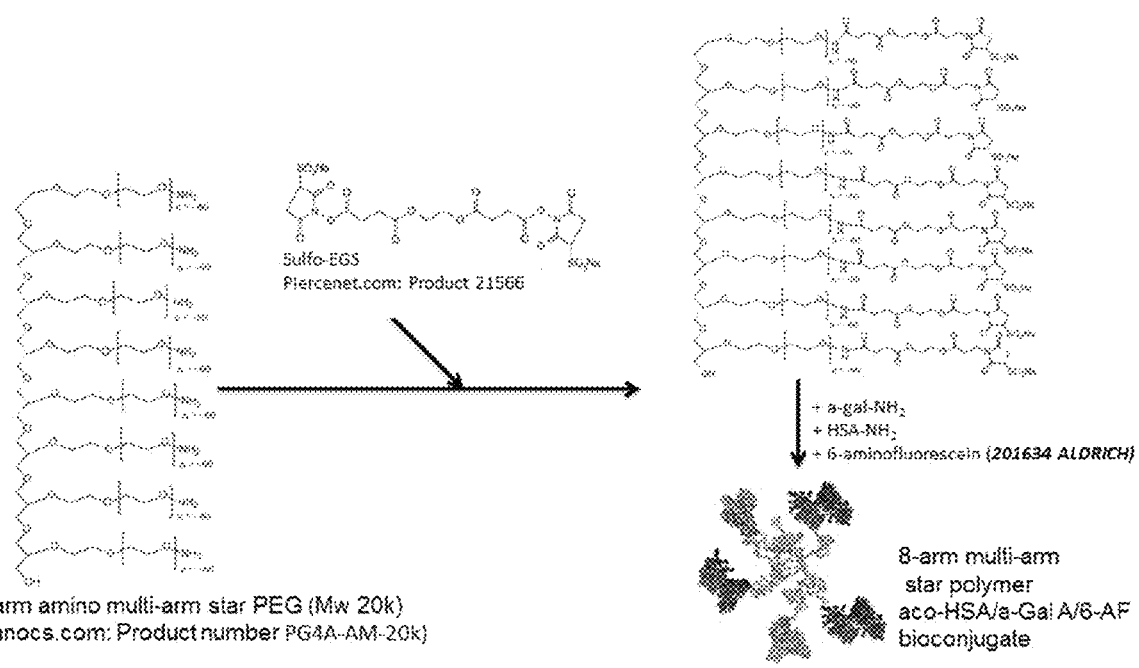
FIG. 6 depicts α-galactosidase A and fluorescently labeled, aconitylated-HSA coupled to multi-arm PEG (amino based coupling).
Figure 7:
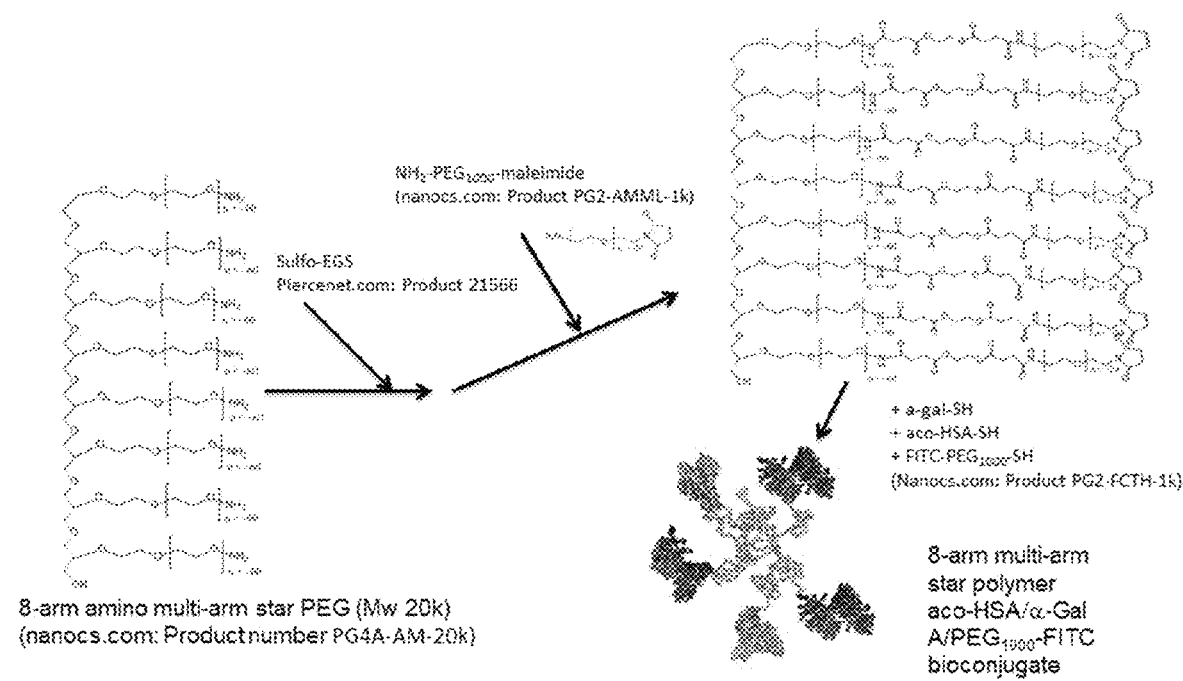
FIG. 7 depicts α-galactosidase A and fluorescently labeled, aconitylated-HSA coupled to multi-arm PEG (sulfhydryl "CYS"-based coupling).
Figure 8:
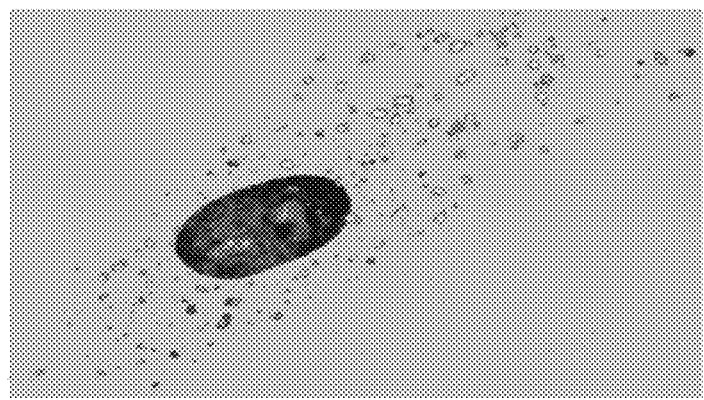
FIG. 8 depicts uptake of α-Gal A using confocal microscopy. Laser-scanning microscope 3D images of normal fibroblasts (GM04390) labeled with LysoTracker (red) to identify lysosomes, DAPI nuclear stain (blue) and α-Gal A with AlexaFluor488 fluorescent tag (Green; yellow represents co-localization) from a LSM 710 Super-Resolution confocal laser-scanning microscope.

The composition comprising the lysosomal enzyme-PEG-SRL assemblies/compositions may be synthesized by any method commonly known in the art. For example a linear PEG linker may be functionalized with NHS and maleimide termini; and conjugated to the primary amines on lysosomal enzyme via the NHS functional group and the thiol groups on the SRL via the maleimide functional group. In a further example, amino functionalized multi-arm star PEG may be reacted with ethylene glycolbis (sulfosuccinimidylsuccinate) (Sulfo-EGS), thereby creating a sulfo-NHS ester functionalized star PEG that may react with amino groups on lysosomal enzyme and SRL. The functionalized star PEG molecule may be reacted with lysosomal enzyme, SRL, and a functionalized fluorophore to create a composition wherein the termini of the star PEG independently comprise lysosomal enzyme, SRL, and a label. An example is depicted in FIG. 3.

When the lysosomal enzyme is α-galactosidase A, α-galactosidase A may be bound to galactose to block disruption of the catalysis. FIG. 3 is provided as an example only, and the composition may comprise different numbers of α-galactosidase A, serum protein, and a label; it may include α-galactosidase A and serum protein only; the serum protein may or may not be labeled.

In another embodiment, lysosomal enzyme is linked to the scavenger receptor ligand by way of a hydrolysable linker. Hydrolysable linkers, or pH labile linkers, are designed to be broken down only in the acidic environment of the lysosome. Other suitable linkers include disulfide-based linkers, which are broken down in the cell where there is a high concentration of thiols, and peptide linkers, which are broken down by intracellular enzymes. Hydrolysable linkers are commonly known in the art. For example, linkers containing amide, hydrazine, or cis-aconityl bonds.

In another embodiment, the composition of the invention further comprises a label. Labels are commonly known in the art. For example, suitable labels include: biotin, enzyme conjugates, and fluorescent.

In preferred embodiment, lysosomal enzyme-acylated SRL conjugate or the lysosomal enzyme-linker-SRL comprises a fluorescent label. Fluorescent labels are commonly known in the art. Suitable fluorescent labels include: fluorescein, rhodamine, coumarin, BODIPY, cascade blue, Lucifer yellow, phycobliprotein, cyanine, lanthanide, quantum dot nanocrystals, and derivatives thereof.

In another embodiment, the fluorescent label is conjugated to the SRL. Conjugation of the fluorescent label to the SRL may be accomplished by any method commonly known in the art. For example, a NHS-functionalized fluorphore may react with an amine group of the SRL.

In another embodiment of the invention, the fluorescently labeled SRL is aconitylated.

In another embodiment, a heterofunctional PEG with a NHS functional group at one termini and a maleimide functional group at another termini is first reacted with an amino group on a lysosomal enzyme; and then reacted with a thiol group on the SRL. In another aspect of the invention, α-galactosidase A is the lysosomal enzyme and may be bound to galactose to block disruption of the catalysis.

In another aspect of the invention, a composition and method for delivering a compound across the blood brain barrier is provided.

The blood-brain barrier (BBB) is a term used to describe the unique properties of the microvasculature of the central nervous system (CNS). CNS vessels are continuous nonfenestrated vessels, but also contain a series of additional properties that allow them to tightly regulate the movement of molecules, ions, and cells between the blood and the CNS. This heavily restricting barrier capacity allows BBB endothelial cells (ECs) to tightly regulate CNS homeostasis, which is critical to allow for proper neuronal function, as well as protect the CNS from toxins, pathogens, inflammation, injury, and disease. Brain endothelial cells (BECs), which form the BBB, are highly polarized cells held together by tight junctions that limit the flow of molecules and ions across paracellular space. The restrictive nature of the BBB provides an obstacle for drug delivery to the CNS, and, thus, major efforts have been made to generate methods to modulate or bypass the BBB for delivery of therapeutics In this aspect, a compound to be delivered across the blood brain barrier is conjugated to a blood brain barrier transporter targeting moiety to provide a conjugated compound. Any method known in the art may be used to conjugate the compound to the blood brain barrier transporter targeting moiety. Some examples of conjugation methods are described above. In one embodiment, the compound is conjugated to a blood brain barrier transporter targeting moiety by way of a hydrolysable linker.

In one embodiment, the blood brain barrier transporter targeting moiety is a ligand that is selective for SR-A3, SR-A5, or SR-BI scavenger receptor. Suitable ligands include AcLDL, OxLDL, β-amyloid, molecular chaperone, ECM, AGE, HDL, or LDL.

In one embodiment, the blood brain barrier transporter targeting moiety is an antibody selective for human insulin receptor or transferrin receptor; or a molecule that is selective for LDL receptor on the blood brain barrier.

As used herein, the term "antibody" refers to any of a polyclonal antibody, a monoclonal antibody, humanized antibodies, non-human species-specific antibodies, synthetic antibodies, single-chain antibodies, a chimeric antibodies, human antibodies, affinity matured antibodies, bispecific antibodies, as well as fragments of such molecules that comprise at least one complementarity-determining region.

The antibody may be a Camelid single domain antibody, or portions thereof. In one embodiment, Camelid single-domain antibodies include heavy-chain antibodies found in camelids, or VHH antibody. A VHH antibody of camelid (for example camel, dromedary, llama, and alpaca) refers to a variable fragment of a camelid single-chain antibody (See Nguyen et al, 2001; Muyldermans, 2001), and also includes an isolated VHH antibody of camelid, a recombinant VHH antibody of camelid, or a synthetic VHH antibody of camelid.

For example, the antibody fragment includes scFv, sdAb, di-scFv. sdAb is a single domain antibody. scFv includes the VH and VL domains of an antibody and is connected by a linker. di-scFv includes two scFv molecules connect by a linker.

A molecule that is selective for LDL receptor on the blood brain barrier includes an antibody, as described above, or a receptor-binding peptide from apolipoprotein E. A receptor-binding peptide from apolipoprotein E includes a 10-50, 10-20, 20-40, 20-50, or 10-30 residue peptide from the NT domain (residues 1-191) of apolipoprotein E (uniprot PO2649).

The blood brain barrier transporter targeting moiety described above is conjugated to a compound. The compound may be a therapeutic, marker, DNA, or RNA.

The therapeutic may be a large molecule therapeutic or a small molecule therapeutic. The therapeutic may be an anti-cancer, anti-inflammatory, anti-bacterial, anti-viral, or anti-fungal drug.

The marker may be a fluorescent marker or a radionucleotide marker. As used herein, a fluorescent marker and fluorescent label may be used interchangeably.

In one embodiment, the compound is α-galactosidase A, α-sialidase, α-mannosidase, β-mannosidase, glycosylasparaginase, α-fucosidase, α-N-acetylglucosaminidase, β-galactosidase, β-hexosaminidase, α-subunit, β-hexosaminidase β-subunit, glucocerebrosidase, arylsulfatase A, saposin B, formyl-glycin generating enzyme, β-galactosylceramidase, iduronate sulfatase, α-iduronidase, heparan N-sulfatase, acetyl-CoA transferase, N-acetyl glucosaminidase, β-glucuronidase, N-acetyl glucosamine 6-sulfatase, N-acetylgalactosamine 4-sulfatase, galactose 6-sulfatase, hyaluronidase, α-glucosidase, acid sphingomyelinase, acid ceramidase, acid lipase, cathepsin K, cathepsin A, tripeptidyl peptidase, or palmitoyl-protein thioesterase.

In a another aspect of the invention, a composition is provided that includes lysosomal enzyme as defined above encapsulated by a liposome, said liposome externally comprising SRL.

Encapsulation of substrates by liposomes is commonly known in the art. For example, the composition of the invention may generally be prepared by the process of combining a lipid composition with a solution of human lysozymal enzyme or an active fragment or derivative thereof, suspension or mixture under conditions suitable for liposome formation with the desired amount of a lysosomal enzyme or an active fragment or derivative thereof encapsulated therein.

For example, liposomes may be generated by first assembling a lipid bilayer formulation comprising 5 mole % DSPE-PEG(2000) maleimide, 94% L-α-phosphatidylcholine (POPC), and 1% DiO lipid tracer (1,1'-dioctadecyl-3, 3,3',3'-tetramethylindodicarbocynanine) to make dried lipid film at 25° C. from chloroform solution. Hydrate 2 mg/ml lipid film in PBS buffer with 2 mg/ml lysosomal enzyme to give loaded multilamellar vesicles, then form 100 nm nominal diameter liposomes by probe sonication. Formed liposomes may range from 30 nm to 1 um in diameter. In a preferred embodiment, the liposomes are 100 nm. In another preferred embodiment, the liposomes are 200 nm. In another preferred embodiment, the liposomes are 300 nm. Unencapsulated lysosomal enzyme is removed by G-100 Sephadex chromatography.

Formed liposomes may then be conjugated with aconitylated SRL fluorescein by surface maleimide groups. 3 mg/ml of HSA and 2 mg/ml liposomes are inclubated at pH 7 and 4° C. A final purification is performed with a G-100 Sephadex column to remove free aconitylated SRL fluorescein.

Further liposome preparation techniques commonly known in the art and are described in Liposomes: A Practical Approach, edited by V. P. Torchilin, Volkmar Weissig Oxford University Press, USA, 2nd edition 2003); which is herein incorporated by reference in its entirety.

The liposome containing the encapsulated human lysosomal enzyme or an active fragment or derivative thereof may be coated with negatively charged SRL using methods commonly known in the art. For example, free thiol from surface cysteines on the SRL is reacted with maleimide groups present on the surface of the liposome (described above) to form a composition comprising SRL bound to the surface of liposomes.

The SRL as used herein, refers to any of the SRL described above.

In a further embodiment of the invention the acylated SRL may be covalently labeled. The label may be fluorescent or nonfluorescent. Such labels are commonly known in the art, and are described herein.

In a further embodiment of the invention, the SRL may be acylated, acetylated or aconitylated. Such chemical modifications are commonly known in the art, and are described herein. In a embodiment, the SRL is HSA.

In another embodiment, the SRLs are negatively charged. Said negative charge may be naturally occurring, or conferred by chemical modification by any method known in the art. For example, said negative charge can be conferred by formaldehyde treatment. In another embodiment, the SRL may be oxidized by chemical modification by any method known in the art. For example, with treatment by $Cu^{2+}$.

Further liposome preparation techniques commonly known in the art and are described in Liposomes: A Practical Approach, edited by V. P. Torchilin, Volkmar Weissig Oxford University Press, USA, 2nd edition 2003); which is herein incorporated by reference in its entirety.

Methods of Use

In another aspect of the invention, a method is provided for the treatment of a lysosomal storage disease. The method includes administering a composition that includes a lysosomal enzyme conjugated to a negatively charged scavenger receptor ligand, as described above, to a mammal in need thereof. In one embodiment, the lysosomal storage disease is caused by deficient lysosomal enzyme. In this specification "treating" refers to inhibiting disease; preventing disease; aiding in the prevention of disease, or combinations thereof.

Deficient lysosomal enzyme is defined as any disease state resulting from the absence of a lysosomal enzyme, deficiency of the enzyme, a non-functional enzyme, or an enzyme with reduced functionality. An enzyme with reduced functionality is defined as an enzyme whose catalytic activity is less than wild type enzyme.

In lysosomal storage diseases, the reduced functionality of the lysosomal enzyme causes a buildup of substrate in the lysosome, such as lipids and glycoproteins. The accumulation of substrate causes the cell to malfunction. Symptoms of lysosomal storage disease can be mild to severe and can include developmental delay, movement disorders, seizures, deafness, and/or blindness. Various lysosomal storage diseases are known in the art. TABLE 2 provides for a list of lysosomal storage diseases and the protein responsible for that disease.

In another aspect of the invention, the method includes administering acylated, acetylated, or aconitylated lysosomal enzyme to a mammal in need thereof.

In a preferred embodiment, the method includes administering aconitylated lysosomal enzyme to a mammal in need thereof. A benefit of the aconitylated lysosomal enzyme is that aconitylation is reversible at the acidic pH of the lysosome, and there is a lack of an immune response to aconitylated proteins.

In preferred embodiment of the invention, the lysosomal enzyme is α-galactosidase A, and the disease is Fabry disease.

In another aspect of the invention, a method of delivering a compound across the blood brain barrier is provided.

TABLE 2

PROTEIN AND CORRESPONDING LYSOSOMAL STORAGE DISEASE

| LYSOSOMAL PROTEIN | LYSOSOMAL STORAGE DISEASE |
|---|---|
| α-galactosidase A | Fabry |
| α-sialidase | sialidosis |
| α-mannosidase | α-mannosidosis |
| β-mannosidase | β-mannosidosis |
| glycosylasparaginase | aspartylglucosaminuria |
| α-fucosidase | fucosidosis |
| α-N-acetylglucosaminidase | Schindler |
| β-galactosidase | GM1-gangliosidosis (MPS IVB |
| β-Hexosaminidase α-subunit | GM2-gangliosidosis (Tay-Sachs) |
| β-Hexosaminidase β-subunit | GM2-gangliosidosis (Sandhoff) |
| GM2 activator protein | GM2-gangliosidosis |
| Glucocerebrosidase | Gaucher disease |
| Saposin C | Gaucher disease |
| Arylsulfatase A | Metachromatic leukodystrophy |
| Saposin B | Metachromatic leukodystrophy |
| Formyl-Glycine generating enzyme | Multiple sulfatase deficiency |
| β-Galactosylceramidase (Krabbe) | Globoid cell leukodystrophy |

TABLE 2-continued

PROTEIN AND CORRESPONDING LYSOSOMAL STORAGE DISEASE

| LYSOSOMAL PROTEIN | LYSOSOMAL STORAGE DISEASE |
|---|---|
| Iduronate sulfatase | MPS II (Hunter) |
| α-Iduronidase | MPS 1 (Hurler, Scheie) |
| Heparan N-sulfatase | MPS IIIa (Sanfilippo A) |
| Acetyl-CoA transferase | MPS IIIc (Sanfilippo C) |
| N-acetyl glucosaminidase | MPS IIIb (Sanfilippo B) |
| β-glucuronidase | MPS VII (Sly) |
| N-acetyl glucosamine 6-sulfatase | MPS IIId (Sanfilippo D) |
| N-Acetylgalactosamine 4-sulfatase | MPS VI |
| Galactose 6-sulfatase | MPS IVA (Morquio A) |
| Hyaluronidase | MPS IX |
| α-Glucosidase | Pompe |
| Acid sphingomyelinase | Niemann Pick type A and B |
| Acid ceramidase | Farber lipogranulomatosis |
| Acid lipase | Wolman and cholesteryl ester storage disease |
| Cathepsin K | Pycnodystostosis |
| Tripeptidyl peptidase | Ceroide lipofuscinosis 2 |
| Palmitoyl-protein thioesterase | Ceroide lipofuscinosis 1 |

The method of the invention includes administering an effective amount of the composition to the mammal in need thereof. Preferably the mammal is a human. An effective amount is defined as an amount sufficient to reduce, prevent, or inhibit the accumulation of lysosomal enzyme substrate in the lysosomes of cells of the mammal. Suitable examples of mammals other than humans include, for example, rabbits, rats, mice, horses, goats, or primates.

A therapeutically effective amount of the composition of the invention as described above may range from about 50 to about 10,000 units enzyme activity per kg body weight per day. For example, when the lysosomal enzyme is α-galactosidase A, a unit of α-galactosidase A activity corresponds to one nanomole of 4-methylumbelliferyl-α-D-galactopyranoside hydrolyzed per hour at 37° C. See Calhoun et al., 1985, Proc. Natl. Acad. Sci. USA 82: 7364-7368. This reference is hereby incorporated by reference in its entirety.

In a preferred embodiment, the therapeutic amounts from about 1 µg to about 2000 µg per kg of body weight per day. The dosage regimen may be adjusted to provide the optimum therapeutic response. For example, several divided doses may be administered daily or the dose may be proportionally reduced as indicated by the exigencies of the therapeutic situation.

A practical advantage is that the active compound may be administered in a convenient manner such as by the oral, intravenous (where water soluble), intramuscular, intravenous, intranasal, intradermal, subcutaneous, or suppository routes. Depending on the route of administration, the active ingredients of the composition of the invention as described above containing pharmaceutical composition may be required to be coated in a material to protect said ingredients from the action of enzymes, acids or other natural conditions.

The active compounds may also be administered parenterally or intraperitoneally. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must preserved against the contaminating action of microorganisms such as bacteria and fungi. The carrier may be a solvent or dispersion medium containing, for example, water, ethanol, polyol (for example, glycerol, propylene glycol, and polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. The preventions of the action of microorganisms may be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions may be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The composition of the invention as described above may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparation should contain at least 1% of active compound. The percentage of the compositions and preparations may, of course, be varied and may conveniently be between about 5 to about 80% of the weight of the unit. The amount of active compound in such therapeutically useful compositions is such that a suitable dosage is obtained. A suitable dosage is any dosage sufficient to achieve a beneficial outcome. Preferred compositions or preparations according to the present invention are prepared so that an oral unit dosage form contains between about 10 µg and 1000 µg of active compound.

The tablets, troches, pills, capsules and the like may also contain the following: A binder such as gum agragacanth, acacia, corn starch or gelatin; excipients such as dicalcium phosphate; a disintegrating agent such as corn starch, potato starch, alginic acid and the like; a lubricant such as magnesium stearate; a sweetening agent, such as sucrose, lactose or saccharin or a flavoring agent such as peppermint, oil of wintergreen, or cherry flavoring. When the dosage form is a capsule, it may contain, in addition to materials of the above type, a liquid carrier. Various other materials may be present as coatings or to otherwise modify the physical form of the unit dosage. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

It is especially advantageous to formulate parenteral compositions in dosage unit form for ease of administration and uniformity of dosage. Unit dosage form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health impaired as herein disclosed in detail.

The composition of the invention as described above, is compounded for convenient and effective administration in pharmaceutically effective amounts with a suitable pharmaceutically acceptable carrier in dosage unit form as hereinbefore disclosed. A unit dosage is any dosage sufficient to achieve a beneficial outcome. A unit dosage form can, for example, contain the principal active compound in amounts ranging from 10 μg to about 1000 μg. Expressed in proportions, the active compound is generally present in from about 10 μg to about 1000 μg/ml of carrier. In the case of compositions containing supplementary active ingredients, the dosages are determined by reference to the usual dose and manner of administration of the said ingredients.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients may also be incorporated into the compositions.

Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

EXAMPLES

The following non-limiting examples further illustrate the invention.

Example 1

Expression and characterization of glycosylated and catalytically active recombinant human α-Gal A. We previously isolated human α-Gal A cDNA and genomic clones, and expressed the cDNAs in bacteria, insect cells, and *Pichia pastoris* derivatives, and we analyzed the effects of carboxyl-terminal deletions on enzyme activity. We reported activity for the recombinant human α-Gal A using the natural in vivo substrate GB3 (trihexosylceramide, ceramide trihexoside; CTH) and the artificial substrates 4-methylumbelliferyl-α-D-galactopyranoside (MUG) and para-nitrophenyl-α-D-galactopyranoside (PNPG). All three substrates will be used for quantitative enzyme assays, along with assays using antibodies to GB3 and lissamine rhodamine ceramide trihexoside in cell culture assays. Fabry fibroblasts in cell culture take up the recombinant α-Gal A produced in insect cells and *P. pastoris* as measured using direct enzyme assays. We also measured the uptake of AlexaFluor488-labeled α-Gal A using a live cell assay with a LSM 880 Super-Resolution confocal microscope with Airyscan and a $CO_2$ incubator.

Reaction of Cis-aconitic Anhydride with α-galactosidase A

A solution of enzyme (α-galactosidase A(α-Gal A)) was prepared at 1.35 mg/ml in 0.95 ml of Buffer A, pH 6.5 (110 mM NaHPO4, 0.22% NaN3, and 0.55 mM PMSF). To this was added 1 mg of cis-aconitic anhydride and stirred in the cold at 4° C. for 1.5 hr. The free anhydride was removed with a Sephadex G25 column.

Activity was measured using the artificial substrate MUG, with modification to use microtiter plates. Briefly, 10 μl of enzyme was mixed with 90 ml of enzyme assay buffer (5 mM MUG, 40 mM of sodium acetate buffer, pH 4.5) at 37° C. and incubated at 37° C. At 0, 10, 30, and 60 min, 10 μl was removed from the incubation mixture and added to 100 ml stop buffer of 0.1 M DAE (Sigma, catalog no. E-1521) in a microtiter plate and the fluorescence was read at excitation of 360 nm and emission of 460 nm. Activity was calculated by averaging the last two readings of the fluorimeter and dividing by the coefficient of the MU standard.

The actual activity of the wild type and modified enzymes were identical within experimental error (57,000 units/ml). Enzyme activity was tested in accordance with Chen et al. 2000.

Example 2

Reaction of Cis-aconitic Anhydride with HSA

The reaction is carried out in PBS buffer with 2 mg/ml HSA-fluorescein and 10 fold excess cis-aconitic anhydride at pH 8.5 at 25° C. for two hours. The aconitylated-HSA-fluorescein product was separated from free label with Sepandex G-25 chromatography.

Example 3

Conjugation of α-galactosidase A to Fluorescently-Labeled Aconitylated-HSA (aco-HSA) Fluorescent Labeling of HSA.

First, HSA was labeled with fluorescein. This reaction was carried out in PBS buffer with 2 mg/ml HSA and 20 fold excess NHS-fluorescein at pH 6.5 at 25° C. for one hour to give a low yield labeling reaction (F/P ratio<2) and leave free —$NH_2$ groups for aconitylation reaction. The HSA-fluorescein product was separated from free label with Sepandex G-25 chromatograhy.

Next, cis-aconitic anhydride aconitylation of HSA-fluorescein was done. The reaction was carried out in PBS buffer with 2 mg/ml HSA-fluorescein and 10 fold excess cis-aconitic anhydride at pH 8.5 at 25° C. two hours. The aco-HSA-fluorescein product was separated from free label with Sepandex G-25 chromatograhy.

α-Gal A-$PEG3_{300}$-maleimide Reaction.

Next, α-galactosidase A is conjugated to $PEG3_{300}$-maleimide. The reaction is carried out in PBS buffer with 2 mg/ml α-Gal A and 20 fold excess SM(PEG)8 (Pierce, catalog number 22108) at pH 8.5 at 25° C. two hours. The α-Gal A-$PEG3_{300}$-maleimide product was separated from free label with Sephadex G-25 chromatograhy.

α-Gal A-$PEG3_{300}$-maleimide/aco-HSA-fluorescein Reaction.

Next, α-Gal A-$PEG3_{300}$-maleimide is conjugated to aco-HSA-fluorescein. The reaction is carried out in PBS buffer with 1 mg/ml to 20 mg/ml concentration of α-Gal A-$PEG3_{300}$-maleimide/aco-HSA-fluorescein at 4° C. for two hours. The α-Gal A-$PEG3_{300}$-maleimide-Aco-HSA-fluorescein product is separated from free aco-HSA-fluorescein with Sephadex G-200 chromatograhy combined with α-Gal A activity assays of fractions collected.

Example 4

α-galactosidase A and Fluorescently Labeled Aconitylated-HSA Coupled to Multi-Arm PEG (Amino Based Coupling).

8-arm amino multi arm star PEG (Mw 20k) (NANOCS) is functionalized NHS using low pH hydrolyzable Sulfo-EGS(Ethylene glycol bis[sulfosuccinimidylsuccinate]) (pierce 21566). 8-arm $PEG_{20,000}$-$NH_2$ (100 mg/ml) was reacted with 20 fold excess of Sulfo-EGS at 25° C. for 30 minutes followed by G-25 Sephadex chromatography to yield 8-arm $PEG_{20,000}$-NH-EGS.

The 8-arm $PEG_{20,000}$-NH-EGS was reacted at 25° C. for 1 hour with a mixture of equimolar mixture of α-gal-$NH_2$ HSA-$NH_2$ at 2 mg/ml protein concentration, followed by treatment with 6-aminofluorescein (0.2 mg/ml in 5% DMSO). Superdex 200 chromatography is used to separate out the resulting bioconjugates with molecular weights larger than 50 kDa.

Example 5

α-galactosidase A and Fluorescently Labeled Aconitylated-HSA Coupled to Multi-Arm PEG (Sulfhydryl "CYS"-Based Coupling)

8-arm amino multi arm star PEG (Mw 20k) (NANOCS) is functionalized with NHS using low pH hydrolyzable Sulfo-EGS(Ethylene glycol bis[sulfosuccinimidylsuccinate]) (pierce 21566). Sulfo-EGS and $NH_2$-$PEG_{1000}$-maleimide functionalization of 8-arm $PEG_{20,000}$-$NH_2$ reaction conditions (all at pH 7.5). 8-arm $PEG_{20,000}$-$NH_2$ (100 mg/ml) was reacted with 20 fold excess of Sulfo-EGS at 25° C. for 30 minutes followed by G-25 Sephadex chromatography to yield 8-arm $PEG_{20,000}$-NH-EGS. This intermediate was reacted with $NH_2$-$PEG_{1000}$-maleimide (10 fold excess) at 25° C. for 2 hours followed by G-50 Sehadex chromatography to yield 8-arm $PEG_{20,000}$-NH-EGS-$PEG_{1000}$-maleimide.

The 8-arm $PEG_{20,000}$-NH-EGS-$PEG_{1000}$-maleimide was reacted at 25° C. for 1 hour with a mixture of equimolar mixture of α-Gal A-SH and HSA-SH at 2 mg/ml protein concentration (native free —SH from cysteines), followed by treatment with FITC-$PEG_{1000}$-SH for 1 hour. Superdex 200 chromatography is used to separate out the resulting bioconjugates with molecular weights larger than 50 kDa.

Example 6

Aconitylation of Human α-Gal A

We synthesized Aco-α-Gal A by reacting the surface lysine residues of purified α-Gal A in buffer at a pH of 7.5 with excess (1 mg/ml) cis-aconitic anhydride. The degree of modification of lysines was assessed by estimating the loss of free amino groups as measured by trinitrobenzenesulphonic acid assay (TNBSA) and the more sensitive fluorescamine assay. TNBSA assay and enzyme assays indicated a decrease in approximately 72% of primary amines with no significant decrease in α-Gal A activity. This indicates successful partial aconitylation of the surface lysines in α-Gal A with minimal effect on enzyme activity, although aconitylation is reversible in vivo.

Aconitylation is Reversible at the Acidic pH of the Lysosome.

Aconitylation is reversible at acidic pH and this will generate a normal and fully active α-Gal A at the low pH of the lysosome after ERT in Fabry disease patients. The effect of pH is illustrated for the reversible aconitylation of ovalbumin (OVA) at pH 5.0 but not at pH 7.4. Chloroquine, an inhibitor of lysosomal acidification, blocked deacylation of aconitylated ovalbumin after lysosomal uptake in vivo.

Example 7

Compare uptake by scavenger, mannose, and M6P receptors alone and in combinations.

The level of aconitylation is varied from low to high as described from an average of 1-20 aconityl groups per dimer. These aconitylated derivatives of α-Gal A with terminal mannose or M6P terminated carbohydrate are used for uptake experiments in the presence and absence of specific inhibitors: mannose, mannose 6-P, and polyinosinic acid, (a specific inhibitor of scavenger receptor uptake). We anticipate that scavenger receptor-mediated uptake, which to our knowledge is untested in combination with other receptors, will be independent and/or synergistic in specific cell types.

Example 8

Uptake of α-Gal A and Aco-α-Gal A in U20S and U20S-SRA cells

Figure 9:
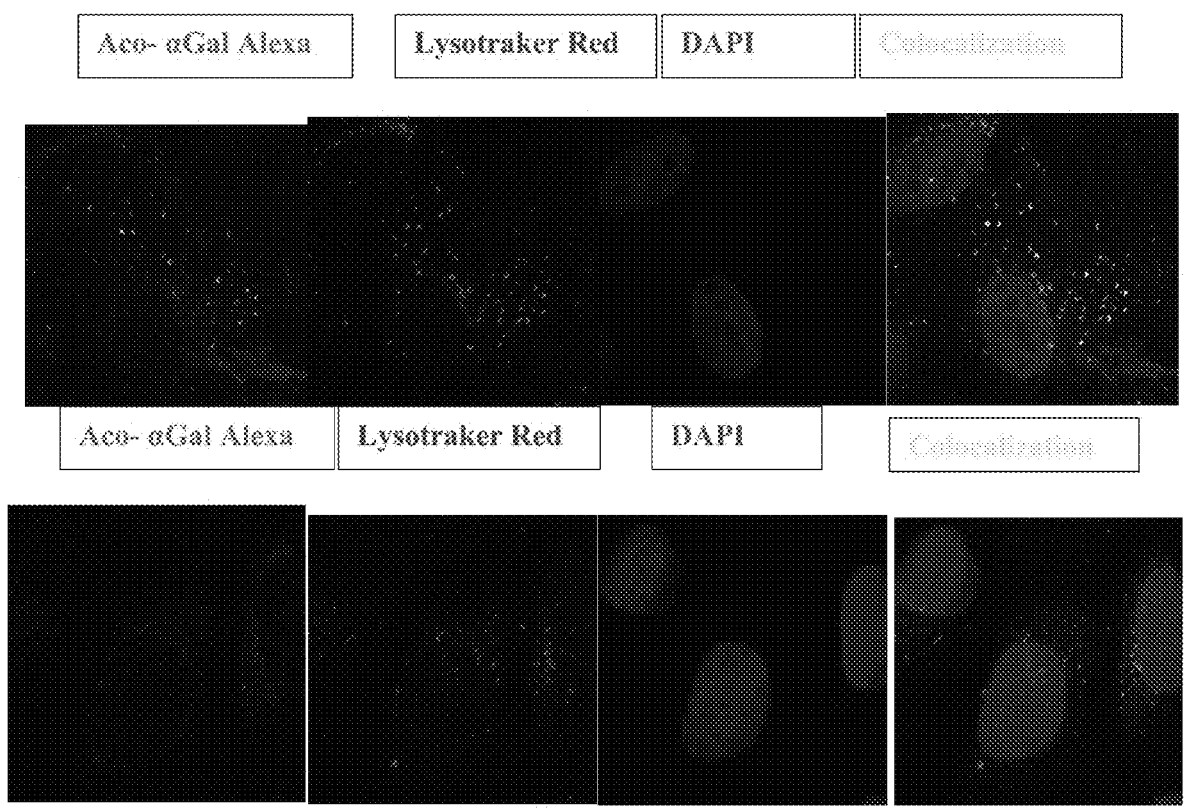
FIG. 9 depicts representative uptake of Alexa-HSA. Uptake of Aco-α-Gal A in U20S-SRA cells (top) and U20S cells (bottom) 2 hr incubation with LSM 710 confocal laser-scanning microscope.

We compared the uptake of α-Gal A, Aco-α-Gal A (FIG. 9), HSA Aco-HSA (aconitylated HSA) in U20S osteosarcoma cells and U20S-SRA cells (isogenic U20S cells expressing the murine scavenger receptor A). Quantitative comparisons (Table below) indicate that aconitylation enhances α-Gal A uptake following a 2 hr incubation comparing U20S cells and U20S-SRA cells. The uptake of Aco-α-Gal A was similar following overnight incubation comparing U20S cells and U20S-SRA cells suggesting that the effect of aconitylation is to increase the rate of uptake. We observed similar uptake patterns with HSA and Aco-HSA. We propose related experiments comparing α-Gal A and Aco-α-Gal A uptake in Fabry endothelial cells and brain-derived endothelial cells using BBB models.

| Totals and Averages (per field) | Number of particles of Alexa-Aco-α-Gal A | | | |
|---|---|---|---|---|
| | 2 hour Incubation | | Overnight Incubation | |
| | U2OS cells | U2OS-SRA Cells | U2OS cells | U2OS-SRA Cells |
| Sum | 49 | 501 | 729 | 646 |
| Average | 12 | 100 | 146 | 129 |
| Std Dev | 9 | 74 | 34 | 59 |

Uptake of Alexa-Aco-α-Gal A in U20S and U20S-SRA cells. Number of particles (above) calculated using ImageJ represents the number of lysosomes in multiple fields with significant Alexa uptake above background (e.g., FIG. 9). Total Alexa fluorescence for these cells gave a similar pattern of uptake.

Example 9

Aconitylated Human Serum Albumin (Aco-HSA) Saturates Scavenger Receptors In Vivo.

A scavenger receptor system present in the mononuclear phagocytic system on endothelial and Kupffer cells is responsible for the uptake and clearance of aconitylated human serum albumin (Aco-HSA). Pharmacokinetic evaluation of Aco-HSA, showed dose dependency attributed to saturation of scavenger receptors on liver and spleen endothelial cells that are responsible for the uptake and elimination of these compounds. The Michaelis-Menten parameters for 125I-Aco-HSA indicate a Vmax (62±8 μg/min/kg) and Km (16±4 μg/ml) for this in vivo mouse system that results in elevated blood levels. These high plasma concentrations (up to 1 mg/ml) did not affect blood coagulation or lymphocyte proliferation, and showed no acute or sub-acute toxicity.

Example 10

Lack of an Immune Response to Aco-HSA

The lack of an immune response to Aco-HSA was indicated by sensitive lymphocyte proliferation assays showing that lymphocyte functions were not significantly altered following immunization of rats with complete Freund's adjuvant for a four-week period. The specific scavenger receptor inhibitors polyinosinic acid and formaldehyde-treated human serum albumin selectively blocked liver and spleen uptake of 125I-Aco-HSA. These results demonstrate the presence of high levels of Aco-HSA distributed throughout the body. Aco-α-Gal A will target diverse sites of accumulation of GB3 substrate in Fabry disease patients (Table 1), including kidneys, lungs, cardiomyocytes, virtually all microvascular endothelial cells, and brain (next section). An efficient and widespread delivery system expected for Aco-α-Gal A can minimize ERT dose and frequency and this, along with aconitylation, will reduce the immune response to α-Gal A.

Example 11

BBB Transport by Scavenger Receptors

Compounds conjugated to a blood brain barrier transporter targeting moiety is tested using a in-vitro BBB endothelial/astrocyte co-culture systems.

Examples of blood brain barrier transporter targeting moieties tested include AcLDL, OxLDL, β-amyloid, molecular chaperone, ECM, AGE, HDL, and LDL, which are ligands for SR-A3, SR-A5, and SR-BI. These moieties are conjugated to α-galactosidase A or a fluorescent marker.

Example 12

Liposomes conjugated to Aco-HSA will be carriers to deliver encapsulated α-Gal A. A protein fusion of α-Gal A to the IgG domain of a monoclonal antibody against the endogenous BBB human insulin receptor or transferrin receptor to carry the fused protein across the BBB is generated and tested in an in-vitro system. Alternatively, α-Gal A is fused to a receptor-binding peptide from apolipoprotein E in order to bind to LDL receptors on the BBB for transcytosis into the CNS.

Example 13

Aco-α-Gal A is tested in a Fabry mouse model to measure half-life in the blood following infusion, tissue distribution, removal of accumulated GB3 substrate, and other organ specific effects present in this mouse model system.

INCORPORATION OF SEQUENCE LISTING

Incorporated herein by reference in its entirety is the Sequence Listing for the above-identified Application. The Sequence Listing is disclosed on a computer-readable ASCII text file titled "Sequence_Listing_1038-136_CIP.txt", created on Nov. 27, 2018. The sequence.txt file is 7.66 KB in size.

What is claimed is:

1. An engineered non-imunogenic lysosomal enzyme comprising: a lysosomal enzyme having at least one cis-aconitic anhydride coupled to at least one surface lysine residue of the lysosomal enzyme.

2. The engineered non-immunogenic lysosomal enzyme according to claim 1, wherein the lysosomal enzyme is α-galactosidase A, α-sialidase, α-mannosidase, β-mannosidase, glycosylasparaginase, α-fucosidase, α-N-acetylglucosaminidase, β-galactosidase, β-hexosaminidase, α-subunit, β-hexosaminidase β-subunit, glucocerebrosidase, arylsulfatase A, saposin B, formyl-glycin generating enzyme, β-galactosylceramidase, iduronate sulfatase, α-iduronidase, heparan N-sulfatase, acetyl-CoA transferase, N-acetyl glucosaminidase, β-glucuronidase, N-acetyl glucosamine 6-sulfatase, N-acetylgalactosamine 4-sulfatase, galactose 6-sulfatase, hyaluronidase, α-glucosidase, acid sphingomyelinase, acid ceramidase, acid lipase, cathepsin K, cathepsin A, tripeptidyl peptidase, or palmitoyl-protein thioesterase.

3. The engineered non-immunogenic lysosomal enzyme according to claim 1, wherein said lysosomal enzyme is α-galactosidase A.

4. The composition of claim 1, wherein said lysosomal enzyme is engineered to have at least one non-wild type surface lysine residue.

5. A method of treating a lysosomal storage disease in a mammal, said method comprising administering to said mammal a therapeutic amount of a pharmaceutical composition comprising the engineered non-immunogenic lysosomal enzyme according to claim 1.

6. The method of claim 5, wherein the lysosomal storage disease is caused by deficient lysosomal enzyme.

7. The method of claim 5, wherein said lysosomal enzyme is a-galactosidase A.

8. The method of claim 5, wherein said disease is Fabry disease.

* * * * *